United States Patent
Kawasaki

(10) Patent No.: US 7,503,763 B2
(45) Date of Patent: Mar. 17, 2009

(54) IN-MOUTH CAVITY TRACING DEVICE

(75) Inventor: Tsugumichi Kawasaki, Tokyo (JP)

(73) Assignee: Casting-In Co., Ltd., Kumamoto (JP)

( * ) Notice: Subject to any disclaimer, the term of this patent is extended or adjusted under 35 U.S.C. 154(b) by 0 days.

(21) Appl. No.: 11/277,965

(22) Filed: Mar. 30, 2006

(65) Prior Publication Data

US 2007/0231771 A1 Oct. 4, 2007

(51) Int. Cl.
*A61C 19/04* (2006.01)
(52) U.S. Cl. .......................... 433/68; 433/69
(58) Field of Classification Search ............ 433/68, 433/69, 55, 56; 33/513, 514
See application file for complete search history.

(56) References Cited

U.S. PATENT DOCUMENTS

| | | | | |
|---|---|---|---|---|
| 2,447,287 A | * | 8/1948 | Smith et al. | 433/69 |
| 2,481,203 A | * | 9/1949 | Davies et al. | 433/69 |
| 2,840,910 A | * | 7/1958 | Ford | 433/69 |
| 2,876,541 A | * | 3/1959 | Jensen | 433/69 |
| 2,994,957 A | * | 8/1961 | McLeod | 433/69 |
| 3,564,717 A | * | 2/1971 | Ennor | 433/69 |
| 4,045,872 A | * | 9/1977 | Arant | 433/55 |
| 4,084,319 A | | 4/1978 | Dragan | |
| 4,304,551 A | * | 12/1981 | Kawasaki | 433/69 |
| 4,892,480 A | | 1/1990 | Levandoski | |
| 4,981,437 A | * | 1/1991 | Wilcox | 433/55 |
| 5,044,950 A | * | 9/1991 | Hobish et al. | 433/69 |
| 5,186,624 A | * | 2/1993 | Gottsleben | 433/69 |
| 5,188,529 A | * | 2/1993 | Luth | 433/68 |
| 5,632,619 A | | 5/1997 | Polz | |
| 5,722,828 A | * | 3/1998 | Halstrom | 433/69 |
| 6,106,285 A | * | 8/2000 | Kwak | 433/68 |
| 6,109,917 A | * | 8/2000 | Lee et al. | 433/73 |
| 6,152,730 A | * | 11/2000 | Wildman | 433/68 |
| 2005/0084817 A1 | * | 4/2005 | Teng | 433/68 |
| 2005/0112523 A1 | * | 5/2005 | Massad | 433/68 |
| 2006/0040232 A1 | * | 2/2006 | Shoup | 433/72 |
| 2006/0127839 A1 | * | 6/2006 | Sellmann | 433/69 |
| 2006/0172254 A1 | * | 8/2006 | Shindo et al. | 433/68 |
| 2007/0264609 A1 | * | 11/2007 | Brunner et al. | 433/69 |

\* cited by examiner

*Primary Examiner*—Ralph A Lewis
*Assistant Examiner*—Sunil K Singh
(74) *Attorney, Agent, or Firm*—Cermak Kenealy Vaidya & Nakajima LLP

(57) ABSTRACT

A tracing device for use in the mouth cavity can include an upper jaw plate, a lower jaw plate, and a coupling tool that connects the above jaw plates. The upper jaw plate can be provided with a guide prop stud, a stud installation pore, a tracing pin, a tracing pin installation pore as well as an auxiliary stud. The lower jaw plate can include a guide tracing table, a connection pore, as well as a movement line formation table. Different structures can be made of a magnetic material or associated with a magnet. A lower jaw inducement guide plate can be made of plastic and have three dimensional slopes, and a guide tracing table can have a tracing plate, and can be freely attachable/detachable to/from the main body of the lower jaw plate.

19 Claims, 17 Drawing Sheets

IN-MOUTH CAVITY TRACING DEVICE

BACKGROUND

1. Field

The disclosed subject matter relates to a tracing device for use in a mouth when center relation and jaw movement are recorded in an odontology clinical. In the in-mouth cavity tracing device, a lower jaw inducement guide plate which can have the shape of three dimensional slopes including plastic, and a guide tracing table which has a tracing board are connected by pressure, and fitted to the main body of the lower jaw plate, and can all be freely detached in use. Also, an in-mouth cavity tracing device can include a lower jaw inducement guide plate shaped in three dimensional slopes having arbitrary angles.

In recent odontology clinical studies, cases of using implantation, and ceramics, etc. as the newest odontology clinical materials, have been increasing. Also, in the in-mouth cavity tracing device, the desire for accurate measurement and recording of the position where a jaw movement, and the jaw itself are steady has been recognized.

Moreover, in terms of maintaining health in the mouth for a long time where odontology clinical mending materials are installed, accurate measurement, and recording of the position where a jaw movement, and the jaw itself are steady can be important in making odontology mending materials.

2. Description of the Related Art

Conventionally, in an in-mouth cavity tracing device, there are several typical devices and methods, including the Check-bite Method, the Pantograph Method, the Chew-in Method, for example, that are used for measuring movements of center relation of the jaw as well as the lower jaw. Among them, the Check-bite Method using the tracing device is the most widely adopted measuring and recording method.

The tracing device used for the Check-bite Method has a tracing pin installed in the upper jaw, and a plane tracing board installed in the lower jaw.

Tracing the horizontal movement line of the lower jaw on the tracing board can be possible by inducing the lower jaw forward and to the side. The movement line of the lower jaw is composed of three lines with one arrow head, and this tracing chart is called the Gothic arch. The point where these three lines intersect is the so-called APEX. Locating the APEX of the Gothic arch traced like this in the center, the horizontal jaw position can be determined, which can also be applied to a patient with missing or no teeth (denture wearers).

When the Gothic arch tracer mentioned above is used for cases of a jaw with teeth, and implantation, it can be traced in case of raising diameter of bite, i.e., a mouth being open wide, since the tracing board is planar.

Moreover, in this Gothic arch tracer, a high diameter of bite is often required, which can be stressful and make a patient's load heavier. Further, in the above condition, it is troublesome that natural movement of the lower jaw cannot be made, thus the correct center position cannot be determined. Consequently, in recording an in-mouth cavity, it is an important condition in determining the correct center position not to raise the diameter of bite.

As for the above-mentioned Gothic arch tracer, lots of troubles were found as listed above, since the position of APEX was difficult to confirm due to tracing in bold lines, and enough clearance space (space for no contact with upper and lower teeth) was typically necessary while recording. Moreover, the recording related to the center relation of the jaw, as well as movement of the lower jaw, are made in the paraffin wax, etc. by Check-bite Method based on the Gothic arch. In order to record precisely the center relation of the jaw, and the movement of the lower jaw, the Gothic arch should be done in high tracing accuracy.

In the in-mouth cavity tracing device shown in the Japanese Patent Publication No. 18053/1984 (U.S. Pat. No. 1,245,692) which is hereby incorporated by reference in its entirety, it is known that accurate recording can be done in the cases where a patient has no teeth or has partial dentures, and is often used in the odontology clinic.

The in-mouth cavity tracing device shown in this patent gazette is composed of the upper jaw plate A shown in FIGS. 6 and 7, the lower jaw plate B shown in FIGS. 9 and 11, and the coupling tool C shown in FIG. 13. It is installed in the mouth cavity as shown in FIGS. 14 and 15, and then tracing of the Gothic arch, and gathering of the Check-bite are done.

The upper jaw plate A as shown in FIG. 6 is placed downward with a projection at almost center to the main body of the upper jaw plate a which is u-shaped. And, it can include the guide prop stud 2 having rotating ball 4 at the edge, and two supplementary studs 3 installed symmetrically downward at the rear edge of the main body of the upper jaw plate "a". Pin device "f" can be installed downward with a projection at the front edge "e" of the main body of upper jaw plate "a" having cylinder maintenance part 24.

FIG. 7 shows the section view of FIG. 6 along line A2-A2. According to FIG. 7, in drawing in the mouth with the drawing device, the above-mentioned prop stud 2 can freely adjust the length of the device in order to induce the jaw movement and to keep the vertical jaw interval distance, and stud fixation screw 8 can fix the guidance prop stud 2 in place where length is adjusted.

Further, drawing pin 1 can be installed such that it is freely detachable in the hollow and cylindrical maintenance part 24 of the above-mentioned pin device "f" in order to draw the Gothic arch. Pin maintenance device "h" can also be installed to fix this drawing pin 1.

FIG. 8 shows a main part of the above-mentioned pin device "f". As shown in FIG. 8, the above-mentioned pin maintenance device "h" can be composed of a pin stopper 5 that is configured to hold the drawing pin 1, elasticity material 6, and stopping screw 7 for the elasticity material. In addition, a spring 23 for the pin can be installed about the drawing pin 1 in order to maintain a downward pressure.

FIG. 9 is a front view of the lower jaw plate B which is shown from the rear side. As shown in FIG. 9, the lower jaw plate B can include the main body of the lower jaw plate "b" and the recording floor connection part "d". The main body of the lower jaw plate "b" can include drawing table 9 for installing drawing plate 9a placed at the head, and guide table 10 for installing guide plate 10a placed at the center.

The record floor connecting part "d" having U-shape can include two tables of movement line formation tables 11 placed at the rear edge in symmetrical relation to each other respectively in order to install movement line recorder 11a. The main body of the lower jaw "b", and the record floor connection part "d" are detachably fixed with the main body of the lower jaw plate fixation screws 25.

FIG. 10 shows the above-mentioned drawing table 9 located at a foremost position in the mouth. The drawing plate 9a is formed on the surface of this drawing table 9. The drawing plate 9a can include plasticizer materials such as polymerization resins that are placed immediately on the surface of the drawing table 9, and it touches the head of the needle of drawing pin 1 installed in the above-mentioned upper jaw plate A, and records the movement of drawing pin 1 as the Gothic arch.

FIG. 11 shows a sectional view of the lower jaw plate B. In the above-mentioned guide table 10, guide plate 10a with processing resins can be installed. The guide plate 10a being formed on the three-dimensional slopes, corresponds with the guide prop stud 2 installed in the above-mentioned upper jaw plate A. In addition, guide plate 10a can record a patient's own incisor line angle, and can induce the jaw movement to record movement lines by touching with the above-mentioned guide prop stud 2 that serves as a sliding guide. The guide plate 10a can be connected with guide table 10 via guide plate fixation screw 26, as shown in FIG. 12.

Movement line record 11a can be formed by putting plasticity materials such as patty silicon rubbers on the above-mentioned movement line formation tables 11. The line movement recorder 11a can record and form, provided that the supplemental stud 3 follows the sculpturing in three dimensions on plasticity materials such as silicon rubbers, etc by inducing patient's jaw with guide prop stud 2 sliding on the incisor line angle recorded on the above-mentioned guide plate 10a.

The coupling tool C shown in FIG. 13 can include connection shaft 14, upper jaw plate supporter 15, lower jaw plate supporter 16, plate interval fixation screw 17, and connection screw 13 that connects lower jaw plate B. The coupling tool C connects upper jaw plate A, and lower jaw plate B, and is used for installation of the upper jaw plate A and the lower jaw plate B in recording floors X, and Y shown in FIGS. 14 and 15. The recording floor X and Y where upper jaw plate A and lower jaw plate B are installed respectively are removed from coupling tool C, and are fixed with adhesive such as cement in the mouth.

However, in a conventional in-mouth tracing device, the pin device "f" has breakdown problems attributed to the elastic material 6 due to complex detaching structures of the tracing plate formation pin 19, the tracing pin 1, and the jaw fixing pin, respectively, used in recording formation processes of the tracing plate 9a, for example, the Gothic arch, the Check-bite.

The main body of the above mentioned guide prop stud 2 is a male screw. In the process of deciding the vertical jaw distance by turning the thread part of the guide prop stud 2, and fixing by tightening the stud fixing screw 8, the length of the guide prop stud 2 is adjusted through the screw structure. However, there is a problem in that the guide prop stud 2 and/or other components can be easily loosened.

Moreover, the guide prop stud 2 is able to be fixed to maintain the decided length by the stud fixing screw 8. However, there is a fault in that it can be easily loosened in the process. For example, loosening can occur during the process of connecting the guide plate table 10 of the lower jaw plate B, and the guide plate 10a with the guide plate fixing screw 26. The guide plate 10a is fixed to the guide table 10 with the guide plate fixing screw 26, and it is able to detach for adjustment. There is also possibilities of medical accidents occurring, for example, dropping screws, or conditioner tools in the mouth because of the small screw size, etc.

The tracing plate 9a is made by using resin with the tracing plate formation pin 19 in the process of forming a record of the tracing plate 9a. However, the operational formation process is insufficient and complex.

Moreover, in the connecting process to adjust the starting position where the horizontal position should be constant, since it is typically necessary to use the connecting shaft 14, the upper jaw plate supporter 16, the plate interval fixation screw 17, and the connecting screw 13 in the connecting process of the upper jaw plate A and the lower jaw plate B, by using the coupling tool C, the operational efficiency therefore is difficult and complex.

It is also difficult to make a plate that is universally appropriate to a patient's mouth cavity (jaw). In addition, shaking is a problem at the time of detaching the guide tracing table and the lower jaw plate connection part from/to the main body of the lower jaw plate. In the device shown in FIG. 1, the detaching of the subcomponent parts is easy because in part, a complex operation such as tightening of screws is not required. In particular, tracing pin 1 and the jaw fixation pin (the same use as the tracing pin 1) can be fixed with magnetic force, respectively, in the installation pore 40.

In addition, detaching of the subcomponents for adjusting the jaw intervals can be easy, and there is substantially no complex operation required. Thus, the time for clinical adjustment is shortened, since the above-mentioned guide prop stud 2 is fixed with a magnetic force associated with the connection pore 27. In addition, the guide plate 10 and trace plate table 9 that have conventionally been separately installed in the lower jaw plate B can be united as the guide tracing table 33, whereby the detaching process can be done at one time, and the detaching can be easily done, since the installation of the lower jaw plate B is fixed with magnetic force associated with the connection pores 36a, and 36b.

Therefore, the detaching in the mouth cavity can be quickly done in many of the processes. For example detaching can occur quickly in the positioning adjustment process as well as the record formation process of the guide plate 10a, the record formation process of the tracing plate 9a, the Gothic arch tracing process, and the Check-bite collection process in the clinic.

SUMMARY

An in-mouth cavity tracing device can include an upper jaw plate, a lower jaw plate, and a coupling tool which connects the above jaw plates. The upper jaw plate can be provided with a connection pore formed downward with an opening to connect a guide prop stud almost at the center of the U shaped main body of the upper jaw plate; a tracing pin installation pore can be formed downward with an opening to install a tracing pin at the point of the front end that extends forward of the main body of the upper jaw plate; and two auxiliary studs to record movement lines can be installed that project in symmetry respectively downward at the rear end of the main body of the upper jaw plate. The lower jaw plate can include a guide tracing table at the center of the substantially U shaped (e.g. semi-circular, V shaped, etc.) main body of the upper jaw plate, and can also include movement line formation tables at the rear end of the U shaped main body of the lower jaw respectively in symmetry. The connection tool can be provided with the upper jaw plate connection part that includes a stud to connect with the upper jaw plate, the lower jaw plate connection part with a stud to connect with the lower jaw plate, and a plate interval fixing screw that connects the upper jaw plate connection part with the lower jaw plate connection part. Part of or the whole of the connection pore, stud installation pore, and tracing pin installation pore in the upper jaw plate, as well as the connection pore installed in the lower jaw plate can be made of a magnetic material.

The term "pore" as used to describe components of the in mouth cavity of the disclosed subject matter is not limited to an opening, which is the embodiment shown in the drawings. Instead, the term "pore" should be considered to be a coupling between two structures such as an opening in a first structure that mates with a post of the second structure or vice versa, a circumferential rib that mates with a similarly shaped male portion of the second structure or vice versa, a post or key of the first structure that mates with a similarly shaped opening on the second structure or vice versa, a plurality of peripheral anchor points or ribs of a first structure that mate with a male shaped portion of a second structure that fits within the anchor points or ribs of the first structure or vice versa, a spline type system, and other similar coupling structures or combinations of coupling structures.

Further, in light of the foregoing, another embodiment of an in mouth cavity tracing device can include a lower jaw inducement guide plate made of plastic having three dimensional slopes, and a guide tracing table having a tracing plate that is attached tightly, and fitted for being freely attachable/detachable.

Further, in light of the foregoing, another embodiment of an in mouth cavity tracing device can include a lower jaw inducement guide plate made of plastic with three dimensional slopes composed with plural plates having angles of 20-50 degrees, which are properly selected, and fitted for being freely attachable/detachable.

Further, in light of the foregoing, another embodiment of an in mouth cavity tracing device can include a lower jaw inducement guide plate made of plastic with three dimensional slopes composed of plural plates having angles of 20-50 degrees. The plates can be properly selected, and fitted such that they are freely attachable/detachable.

Further, in light of the foregoing, another embodiment of an in mouth cavity tracing device can include a guide tracing table, and the lower jaw plate connection part can be installed in the main body of the lower jaw plate. Two pins can be installed at the front and back of a ditch located by the side wall of the lower jaw plate connection auxiliary device.

Further, in light of the foregoing, another embodiment of an in mouth cavity tracing device can include a guide tracing table, and the lower jaw plate connection part can be installed in the main body of the lower jaw plate. Two pins can be installed at the front and back of a ditch located by the side wall of the lower jaw plate connection auxiliary device.

Detaching of subcomponent parts of the above-described device can be easy, and a complex operation such as tightening of screw(s) is not required, since the above-mentioned tracing pin 1, and the jaw fixation pin (the same use as the tracing pin 1) can be fixed with magnetic force, respectively, in the installation pore 40.

Detaching for adjusting jaw intervals can also be easy, and there is no complex operation required, thus the time for clinical adjustment can be shortened, since the above-mentioned guide prop stud 2 is fixed via a magnetic force associated with the connection pore 27. In addition, the guide plate 10 and trace table 9 that have conventionally been separately installed in the lower jaw plate B can be united as the guide tracing table 33, wherein the detaching process can be done at one time, and the detaching can be easily done, since the installation with the lower jaw plate B is fixed via magnetic force associated with the connection pores 36a, 36b.

Therefore, the detaching process can be quickly done in the mouth cavity in the positioning adjustment process. In addition, the record formation process of the guide plate 10a, the record formation process of the tracing plate 9a, the Gothic arch tracing process, and the Check-bite collection process can all be more quickly accomplished.

In the tracing plate 33b that is placed forward of the above-mentioned guide tracing table part 33, an electrical current passing through the trace pin 1 when it contacts the metallic trace plate part 34 is able to be detected. And, when a small hole in the Check-bite collection process can not be confirmed by interruption of the front teeth, it can be confirmed by the electric detector 200 (see FIG. 16) with lights, buzzer sounds, etc.

In addition, the upper jaw plate A, and lower jaw plate B can be connected with the coupling tool C. Thus, the connection process (which adjusts the starting position that is assumed to be constant in the horizontal position in the upper and lower sides), the adjustment process, and the connection release process can be easily operated by detaching various subcomponents by simply overcoming magnetic force connections.

Also, since the coupling tool C can be separated from the upper jaw plate connection part 29, and from the lower jaw plate connection part 30 by loosening the plate interval fixing screw 17, connection release can be done in a short time.

The pins can be made of magnetic material for preventing the above noted problems in the mouth cavity, since in the past, the screws were clamped by the hand, and were integrated on the resin plate by using a lot of screws in the in-mouth cavity tracing device.

In the in-mouth cavity tracing device, the tracing work in the mouth can be done safely, surely and easily, since the lower jaw inducement guide plate can be made of plastic, having a shape of 3D (three dimensions) on the slope, and the guide tracing table which has the tracing plate can be attached with pressure to the main body of the lower jaw plate, fitted, and freely detachable in the use thereof. Moreover, the tracing work in the mouth can be done safely, certainly, and easily in the in-mouth cavity tracing device since it can assume various angles arbitrarily (properly) by matching the lower jaw inducement guide plate to a patient's mouth.

Moreover, in the in-mouth cavity tracing device, ditches can be installed on the side wall of the lower jaw plate connection part assistance tool with two pins placed at the front and behind to prevent or eliminate shaking between the main body of the lower jaw plate, the guide tracing table, and the lower jaw plate connection part, and thus smooth detaching of these parts can be accomplished. The upper jaw plate can be adhered to the palate tightly, and the tongue can be prevented from pressing by locating the lower jaw plate upward, provided that the upper jaw plate and the lower jaw plate are to be U-shaped. Further, since the patient's tongue can be put in the hollow part of the lower jaw plate, it is possible to prevent the patient's tongue from being pressed by the lower jaw plate, and to also prevent the lower jaw plate from being lifted up by pressure of the tongue, which enables a precise measurement record.

Since a part or the whole of the connection pore installed in the above-mentioned upper jaw plate, the stud installation pore, the installation pore of the tracing pin, and the connection pore installed in the above-mentioned lower jaw plate can be formed with magnetic material or associated with a magnetic force, and screws are not necessary, the tracing operation in the above-mentioned in-mouth cavity can be easy and can be done in a short time.

Moreover, the materials such as pins can be made of a magnetic material for preventing loss or dropping of the pins in the mouth cavity. Whereas, in the related art, screws are clamped by hand, and integrated on the resin plate by using a lot of screws.

In concrete terms, detaching processes can be easily accomplished, and a complex operation such as tightening of screws in each exchange is not required, since the tracing pin, and the jaw fixing pin (tracing pin used together) can be fixed respectively to the tracing pin installation pore via magnetic force.

Since the guide prop stud can be fixed by magnetic force associated with the connection pore, it is easy to detach them for adjusting jaw intervals. The time required for clinical adjustment can be shortened because complex operation is not required.

In these connection release processes, the upper jaw plate connection part and the lower jaw plate connection part can be separated by loosening the plate interval fixing screw, and connection release can be done in a short time. In addition, the guide table, and the tracing table can be combined together as the guide tracing table, which is separately installed in the lower jaw plate in the conventional art, whereby the detaching process can be done at one time, and the detaching process is easy because installation with the lower jaw plate can be accomplished by fixing with the magnetic force associated with the connection pore. Therefore, each subcomponent in the mouth cavity can be quickly detached in the positioning process. Other processes are also simplified and made easier, including the record formation process of the guide plate in the clinic, the record formation process of the tracing plate, the Gothic arch tracing process, and the Check-bite collection process, for example. Moreover, in the tracing table placed forward of the guide tracing table, electrical connection of the tracing pin and metallic tracing plate is able to be detected. Therefore, when a small hole in the Check-bite collection process cannot be confirmed by interruption of the front teeth, it can be confirmed by an electric detector via lights, buzzer sounds, etc. (see FIG. 16).

BRIEF DESCRIPTION OF THE DRAWINGS

The above and other aspects and features of the disclosed subject matter will become more apparent from the following detailed description when taken in conjunction with the accompanying drawings, in which:

FIG. 1(a) shows an embodiment of the upper jaw plate A, FIG. 1 (b) shows an embodiment of the lower jaw plate B, and FIG. 1 (c) shows an embodiment of the coupling tool C, respectively;

FIG. 5(b) shows a bottom view of the lower jaw plate B of FIG. 1.

DESCRIPTION OF EXEMPLARY EMBODIMENTS

Figure 1:
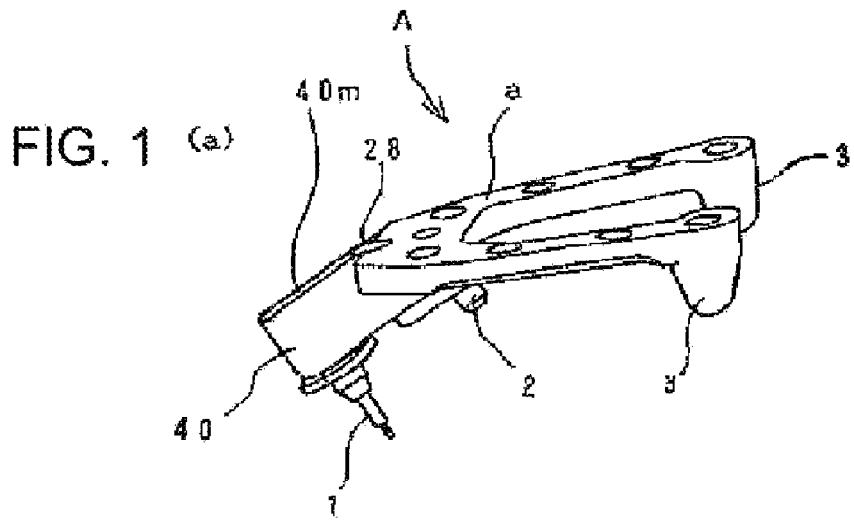
FIGS. 1 (a)-(c) are perspective views of portions of an embodiment of an in-mouth cavity tracing device according to the disclosed subject matter.
Figure 1:
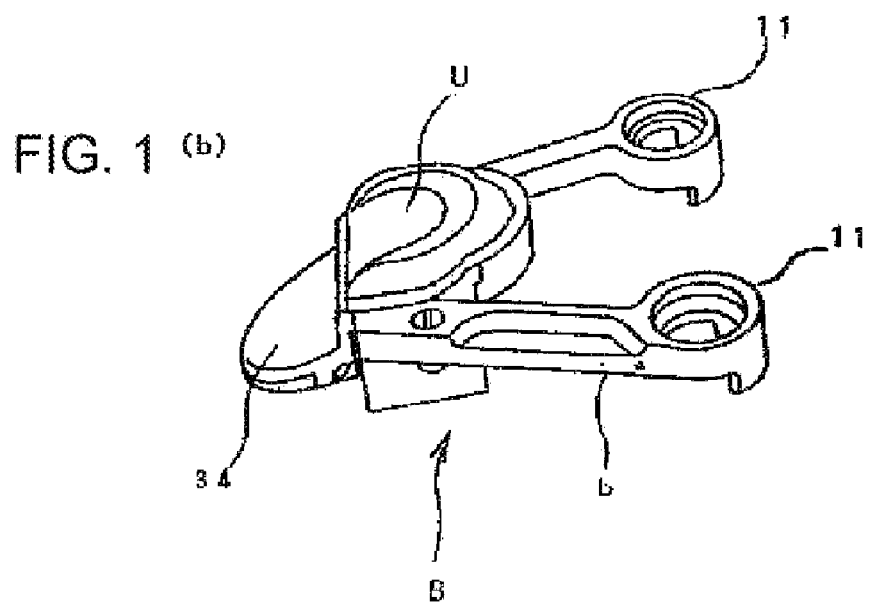
Figure 1:
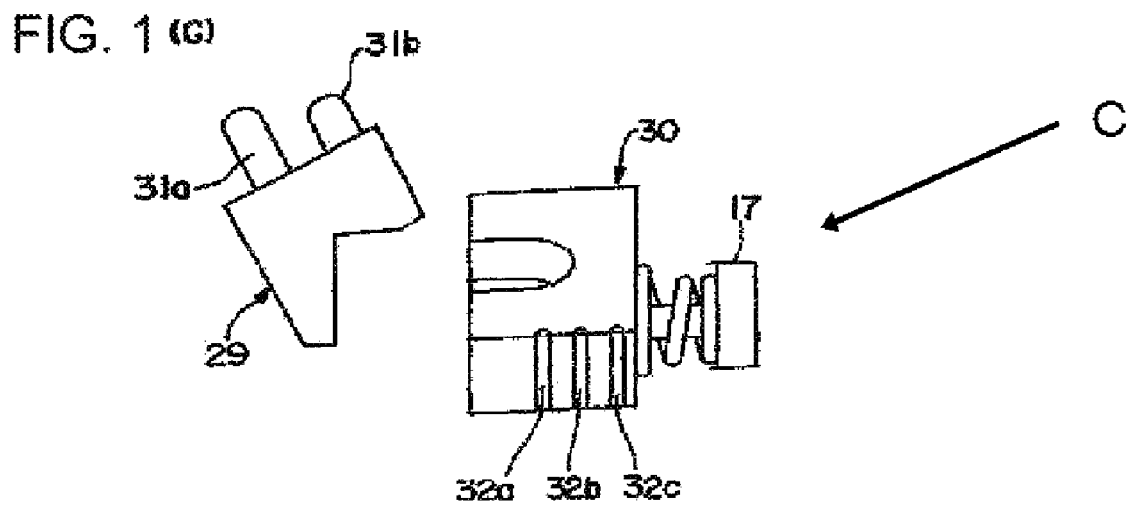

Embodiments of the disclosed subject matter will now be described in detail with reference to FIGS. 1 to 7. The same reference numerals, etc. are used in the embodiments to refer to the same or similar structures and detailed explanation thereof is omitted.

Since the embodiments mentioned below are suitable, and concrete examples of the disclosed subject matter, certain features are technically fixed. However, the scope of the disclosed subject matter is not limited to the particular embodiments or the specific structures for each embodiment.

First of all, a summary outline of the disclosed subject matter is described as follows. The jaw-relator can include the upper jaw frame (plate), the lower jaw frame (plate), and the coupling tool that connects these jaw frames (plates) and locates them to the starting position in the mouth cavity. The upper jaw frame (plate) is installed in a bite floor of the upper jaw by, for example, an immediate polymerized resin, and the lower jaw frame (plate) is installed in a bite floor of the lower jaw.

A procedure for using the in mouth cavity device described above can be as follows.

(1) Selecting a lower jaw inducement guide plate appropriate for a patient's mouth cavity, i.e. the lower jaw inducement guide plate which has arbitrary angles, and is fitted to the main body of the lower jaw plate.

(2) Determining the position of occlusion by using tracks and putting out the patient's jaw frontward, and moving it. Thus, the tracks are drawn on the tracing plate with a pointed pin (for example, a thin needle shape).

(3) Removing the recorded tracing plate and bored pore on the tracks, whereby the position is determined, and the patient can relax their jaw.

(4) That is, the upper needle enters into the pore deciding the position, whereby boring into the pore, and the needle breaks out a part of the resin, and comes in contact downward, and enables confirmation by turning on electricity.

This can take record of the tracing in the mouth cavity without touching teeth.

The jaw-relator can be installed as follows.

(a) Disassembly and assembly can be done with the coupling tool and connection screws to locate the upper jaw frame (plate) and the lower jaw frame (plate) at the starting position in the mouth cavity.

(b) Before the installation work on the bite floor in the mouth cavity, the upper jaw frame (plate), and the lower jaw frame (plate) are connected with the coupling tool, and located at the starting position.

(c) The above-mentioned connection screw is taken apart from the upper jaw frame (plate), and the lower jaw frame (plate) when releasing it. During connecting with the coupling tool, firstly the upper jaw frame (plate) is put temporarily on the bite-floor, at which time the polymerized resin is used at once.

(d) Next, the bite machine is shut, and the lower jaw frame (plate) is put temporarily on the bite-floor under the shutting condition. Right after the polymerized resin stiffens, the connection screw of the coupling tool is released by the special driver.

(e) When the above-mentioned connection screw is released, the bite-machine can be opened without difficulty. Afterwards, the top and bottom of the coupling tool parts are detached. Instead, the tracing pin, and guide prop stud are inserted into the upper jaw frame (plate). The guide tracing table is set in the lower jaw frame (plate).

(f) The above-mentioned guide tracing table is connected with the main body of the lower jaw frame by fitting with the magnet (or construction of magnetic material), and pin, and can be detached freely. Moreover, the detachable tracing plate, and lower jaw inducement guide plate can be installed in the guide tracing table using a one-touch operation. As for a method of maintaining the bite-floor in the mouth cavity, it differs from case to case. In general, resin-coping, and ball-clasp can be used.

In a case of implantation, by using a temporary cylinder, etc., the working model, and the bite-floor in the mouth cavity can be precisely fixed.

In addition, an embodiment of the in-mouth cavity tracing device is explained in detail as follows. The embodiment of the in-mouth cavity tracing device shown in FIG. 1 is composed of the upper jaw plate A having a three-dimensional shape that is similar to a curve of the palate, and also has a U-shape that is narrow in width, hollowed from a center to a rear part of the device. The lower plate B can also have a U-shape that is narrow in width, hollowed from a center to a rear part of the device. Coupling tool C can be provided to connect these plates.

The in-mouth cavity tracing device, including the lower guide plate made of plastic that includes three-dimensional slopes, and the guide tracing table including tracing plate are attached by pressure to the main body and fitted. This feature allows the tracing work in the mouth cavity to be done safely, precisely, and easily as well.

Figure 2:
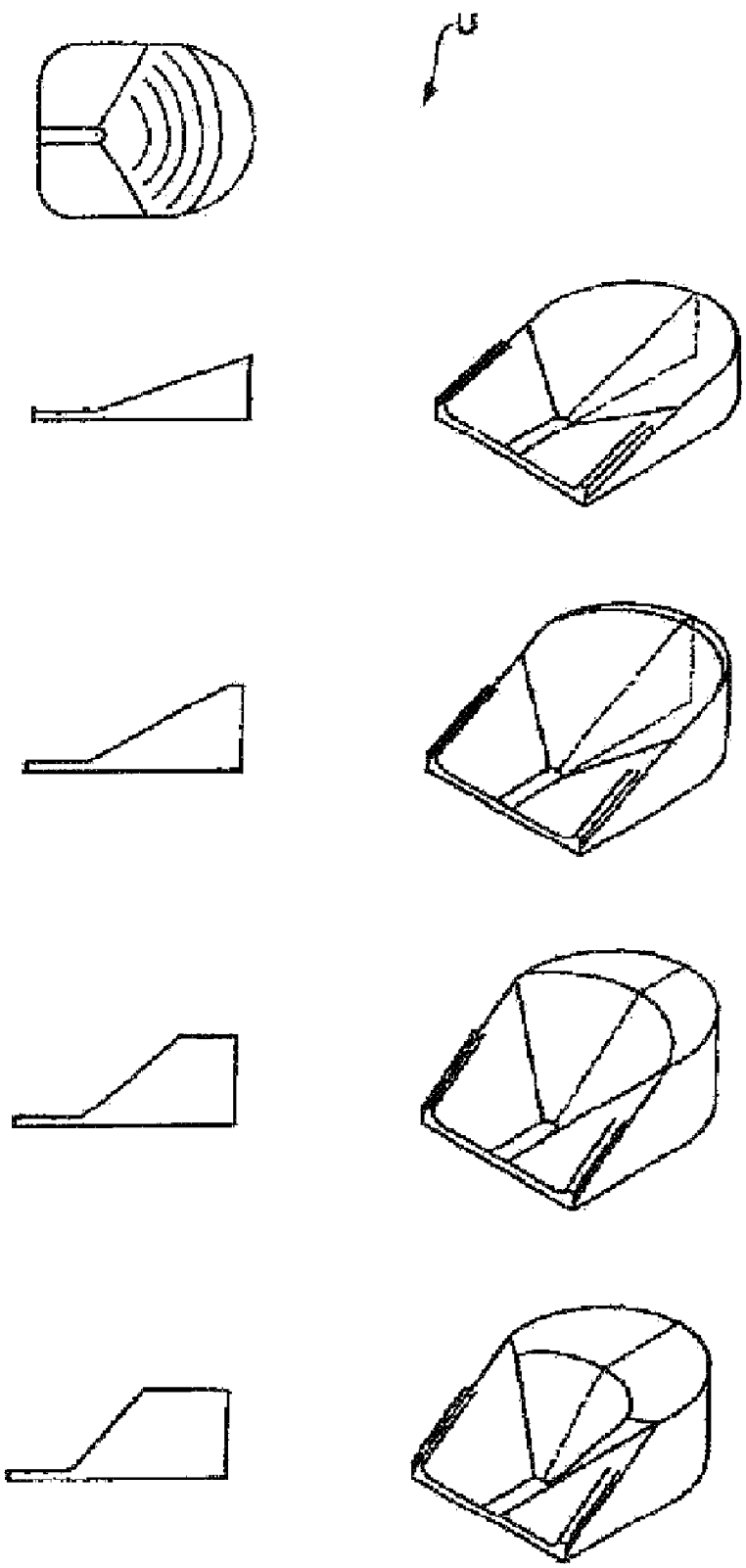
FIG. 2 is a perspective view showing various lower jaw inducement guide tables U of the disclosed subject matter.

In FIG. 2, U is the lower jaw inducement guide plate, that can be freely detachable, made of plastic, used as a guide for inducing the lower jaw, and can have the shape of three-dimensional slopes. It can select the right angle according to the mode of patient's lower jaw from four kinds of angles, i.e. 20°, 30°, 40°, 50°. Therefore, since the lower inducement guide plate U can assume angles arbitrarily according to the patient's palate, the tracing work in the mouth cavity can be done safely, precisely, and easily as well.

Figure 3:
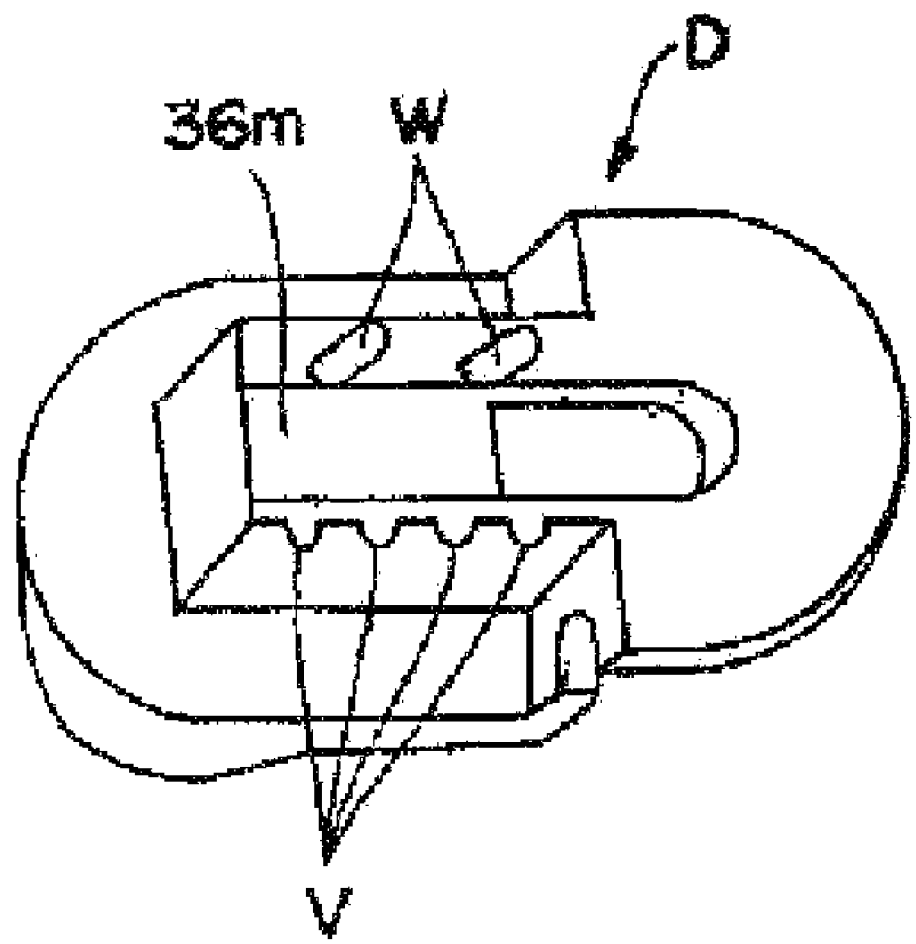
FIG. 3 is a perspective view showing an embodiment of a connection auxiliary tool D of a guide trace table of the disclosed subject matter.

FIG. 3 shows the supplementary tool D which detaches the guide tracing table, and lower plate connection part C, such as those shown in reference numbers 9-11, to the main body of the lower jaw plate. A ditch V can be installed in the sidewall of the lower jaw plate connection part, and two pins W can be installed at the front and rear part. A magnet 36m can provide a connection force. As a result, there is little or no shaking between the main body of the lower jaw plate "b", guide tracing table, and lower jaw plate connection part C. Thus, a smooth detaching operation can be accomplished.

By making the above-mentioned upper jaw plate A, and lower jaw plate B in a U-shaped mode, while the upper jaw plate A can be attached tightly to the palate, the lower jaw plate B is placed upward, and thus the tongue can be prevented from pressing upwards. Moreover, it is possible to place the patient's tongue in the hollow part of the lower jaw plate B, which prevents the tongue from pressing on the lower jaw plate B, and also prevents the lower jaw plate B from being lifted up by pressure of the tongue at the time of recording.

Figure 4:
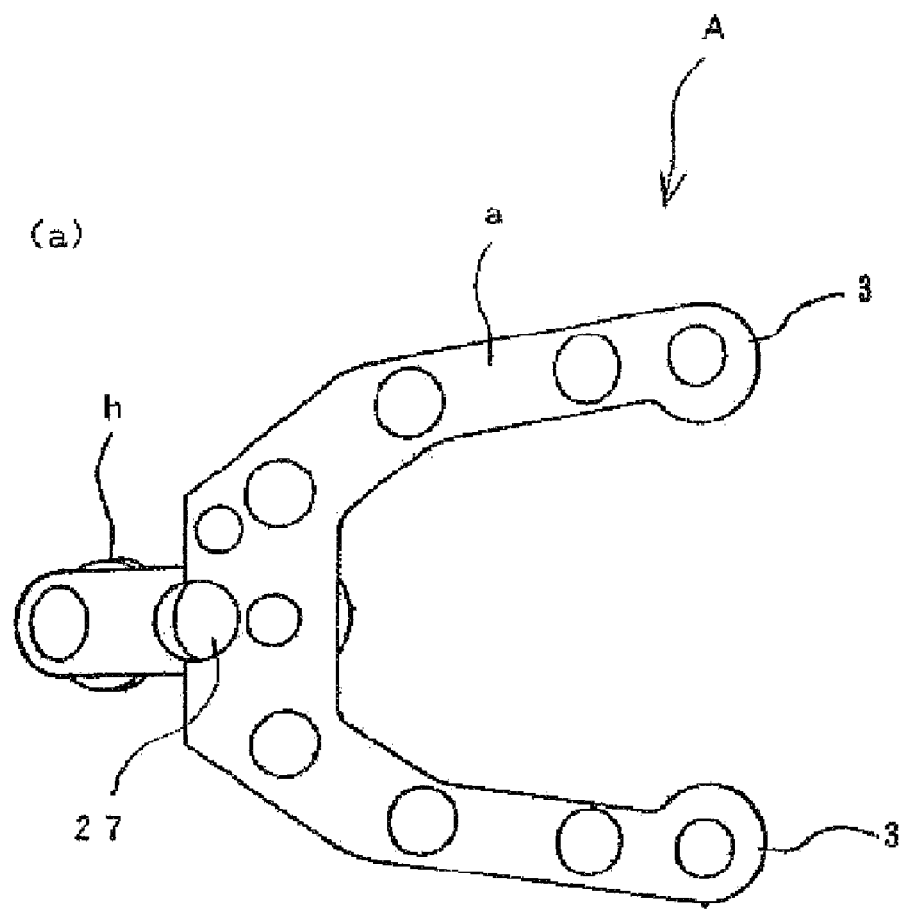
FIG. 4 (a) shows a plane view of the upper jaw plate A of FIG. 1, and FIG. 4 (b) shows a bottom view of the upper jaw plate A of FIG. 1.
Figure 4:
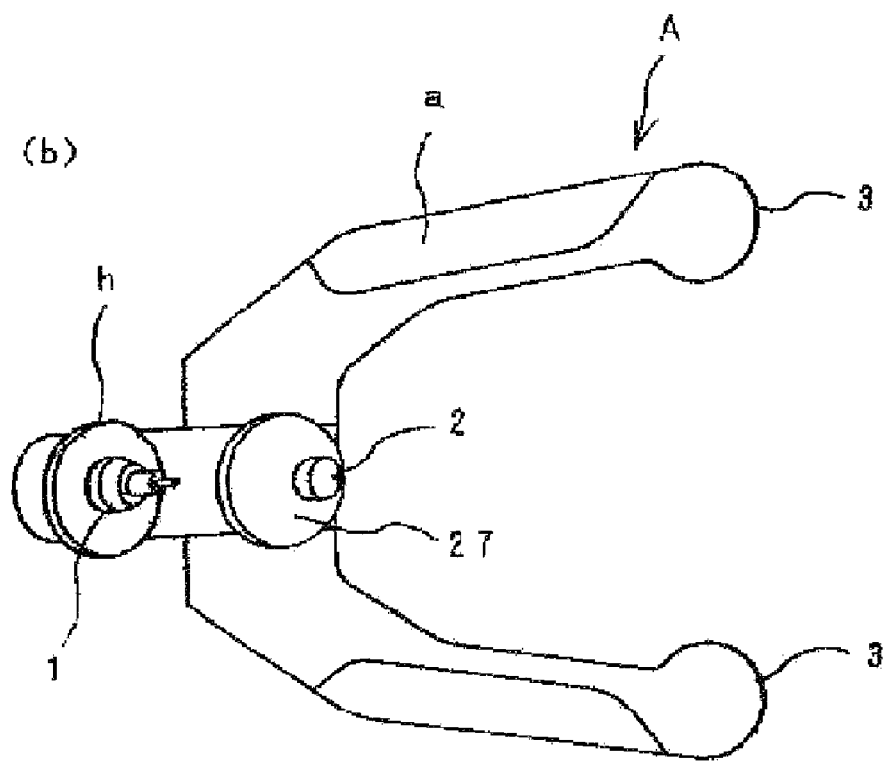

As shown in FIG. 1, and FIGS. 4 (a), (b), the above-mentioned lower jaw plate A can include the connection pore 27 that is made of magnetic material (or associated with a magnetic force from a nearby magnet), and is open downward to connect the guide prop stud 2 at an almost center position of the main body "a" of the upper jaw plate. The stud installation pore can be made of a magnetic material (or associated with a magnetic force from a nearby magnet) and be open downward to connect the coupling tool C. The tracing pin installation pore 40 can be made of magnetic material (or associated with a magnetic force from a nearby magnet such as magnet 40m) and can be open downward to install the tracing pin 1 at the edge of the front part "e" extended forward of the main body "a" of the upper jaw plate. The movement line formation assistance studs 3 can be placed downward and in symmetry with projections at the edge of the rear part of the main body "a" of the upper jaw plate to record two movement lines.

The tracing pin 1 can be a pin for tracing the Gothic arch, and can be fixed via magnetic force to prevent it from falling into the mouth cavity. The tracing pin 1 usually varies in three kinds of length, and the tracing pin moves up and down with springs or other elastic member influence. At the time of biting collection, the tracing pin 1 is fitted to the tracing plate, and the lower jaw position is fixed, and stabilized.

The tracing plate is a plate where the Gothic arch is actually traced, and a hole is bored for the lower jaw to be locked after tracing of the Gothic arch. And, the guide prop stud 2 is a stud for inducing the lower jaw movement while maintaining high diameter biting, and a ball bearing can be used to make movement smooth. Further, the guide prop stud 2 can be made of magnetic material (or associated with a magnetic force from a nearby magnet) so as not to fall into the mouth cavity, and can vary in three kinds of length.

The guide prop stud 2 shown in FIG. 1 has the rotation ball 4 at the edge, which can be fixed to the above-mentioned connection pore 27 with magnet being detachable, and can touch the guide table part 33a in the lower jaw plate B in the above-mentioned guide plate 10a formation process, the movement line recording formation process, the tracing plate formation process, and the Gothic arch tracing process, and forms tracks on the plastic material, and induces the jaw movement by sliding on the guide plate 10a.

The movement line formation assistance studs 3 (supporting stud) can also have a rotation ball 4 at an edge thereof, touch the movement line formation tables 11 of the lower jaw plate B in the movement line recording formation process, and make movement line recording 11a by forming tracks on the plastic material 9.

The movement line formation assistance studs 3 can also induce the jaw movement by sliding on the movement line records 11a of the lower jaw plate B in the tracing plate formation process, and the Gothic arch tracing process. These supporting studs 3 can record 3D tracks of the lower jaw movement on the patty silicone. The tracing pin 1 can be inserted in the tracing pin installation pore 40 made (or associated with) a magnetic material, and can be detachably fixed. The installation length of the tracing pin 1 can be easily changed by exchanging with a pin having different length. The tracing pin 1 is installed in this tracing pin installation pore 40 in the Gothic arch tracing process, and the jaw fixation pin (used together with the tracing pin 1) can be installed in the Check-bite process. As mentioned above, it is easy to detach, and exchange pins used in each process.

Figure 5:
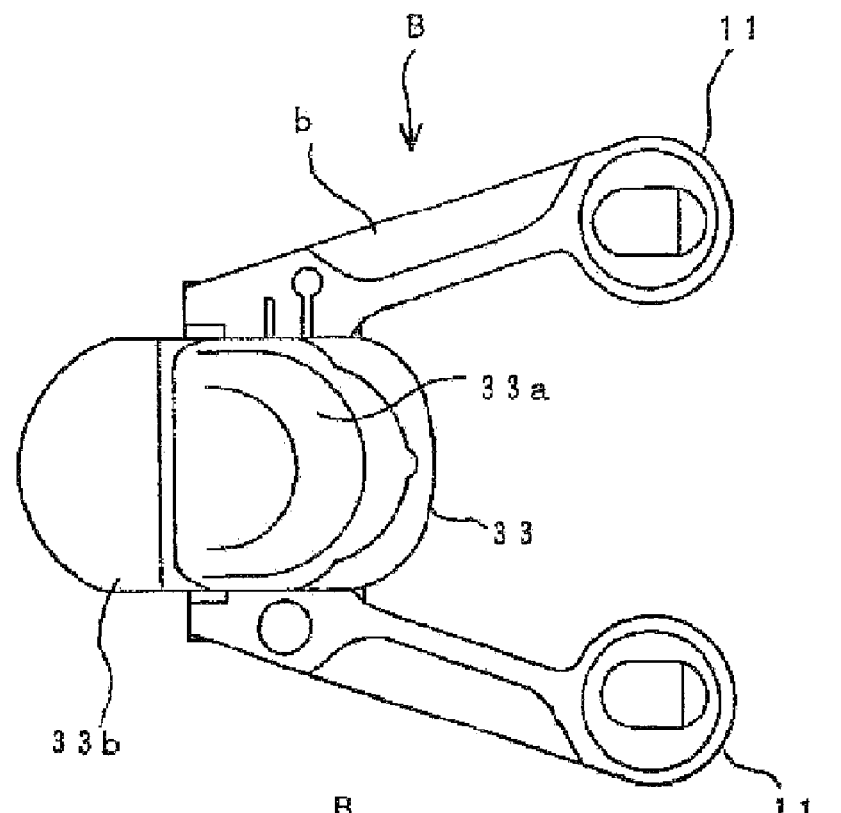
FIG. 5 (a) shows a plane view of the lower jaw plate B of FIG. 1.
Figure 5:
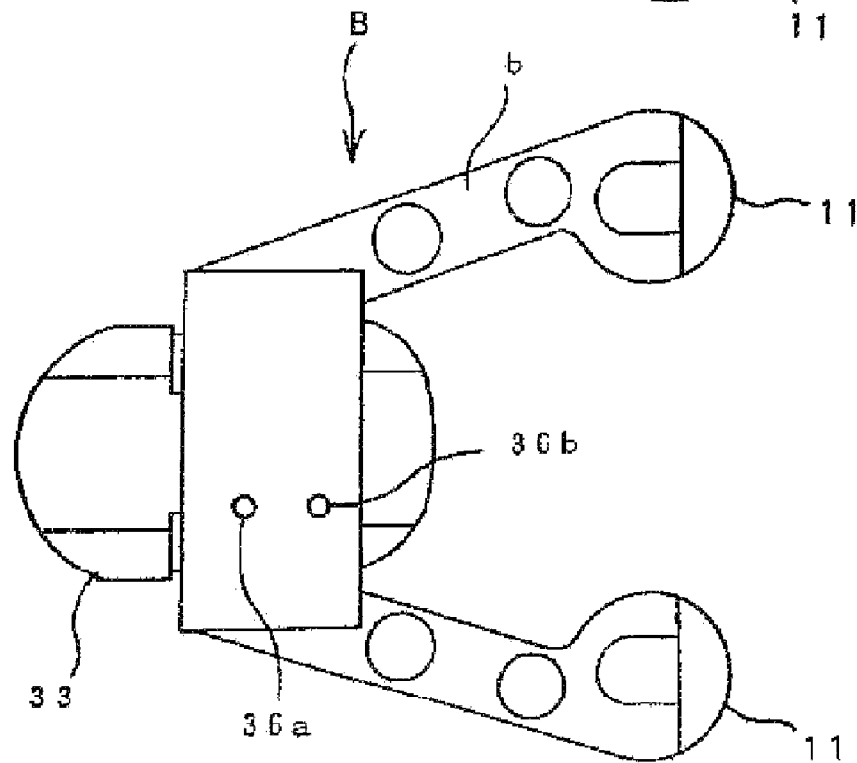
Figure 6:
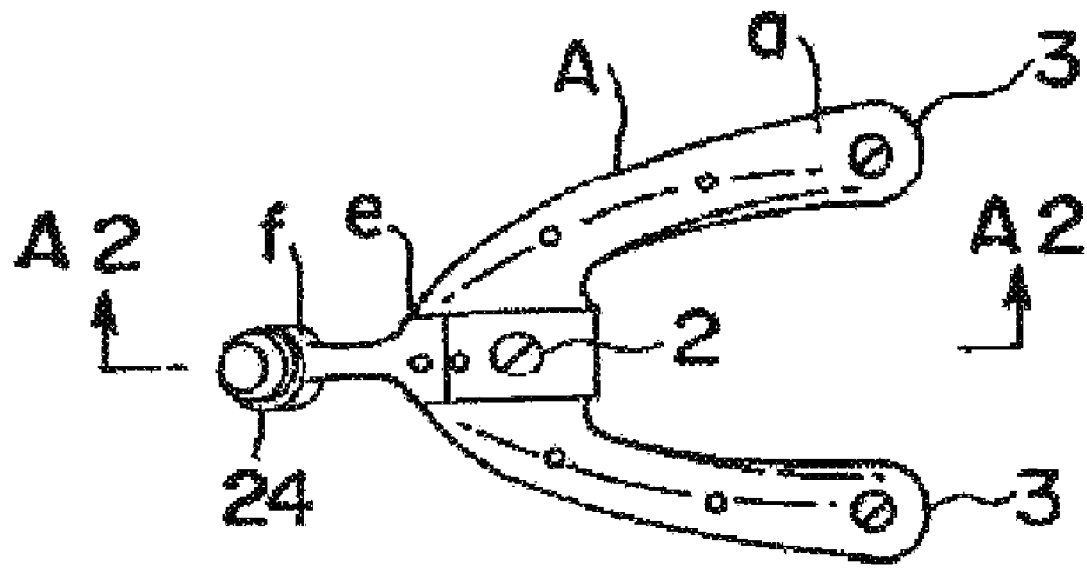
FIG. 6 is a plane view of the upper jaw plate A of the related art.
Figure 7:
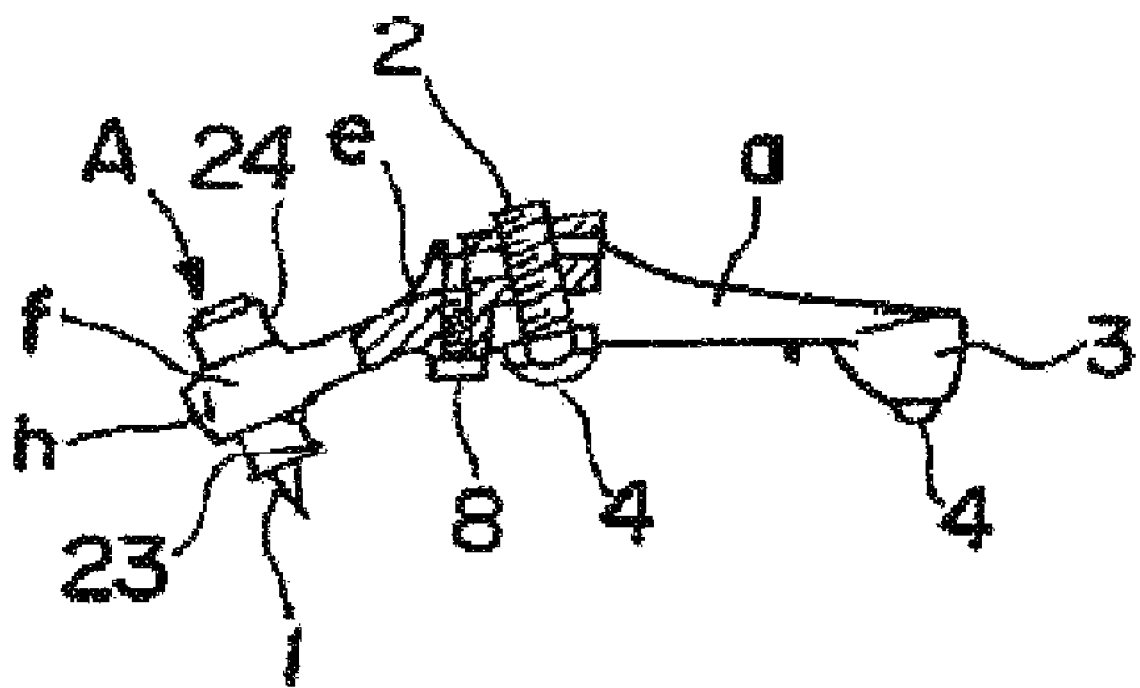
FIG. 7 is a sectional front as viewed along line A2-A2 in FIG. 6.
Figure 8:
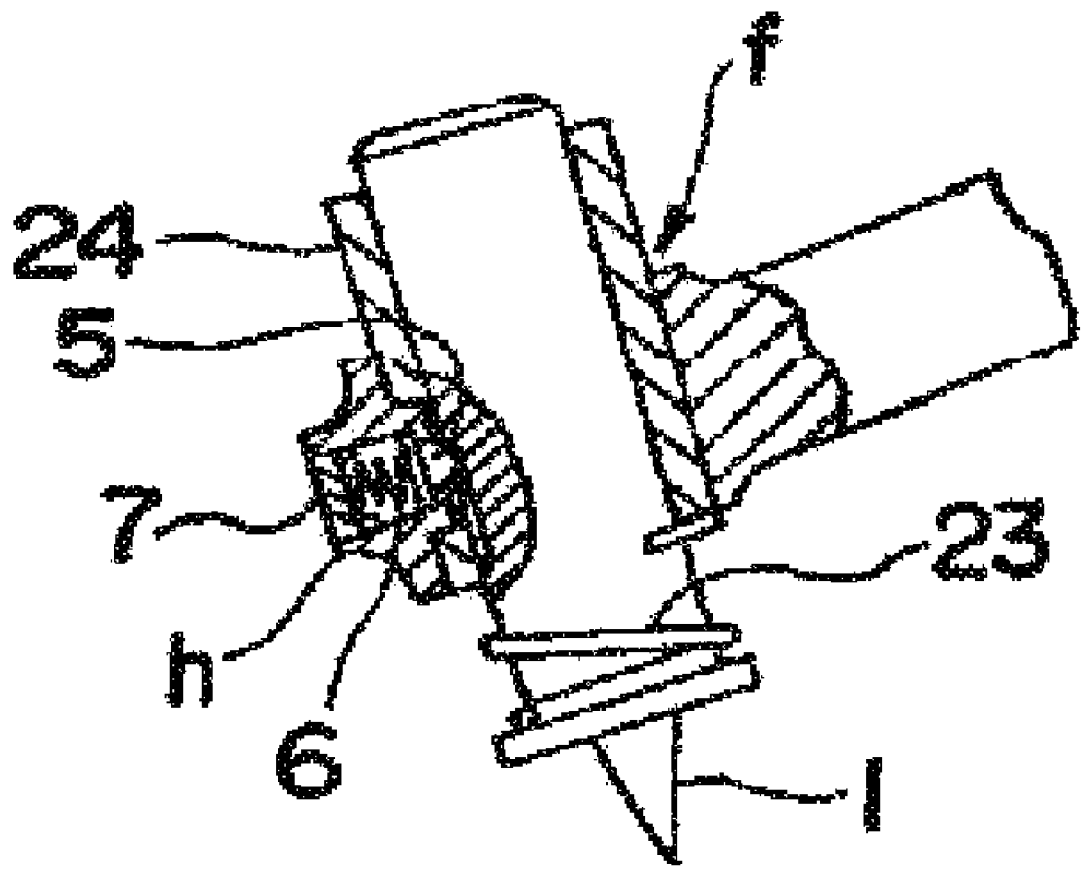
FIG. 8 is a partial-expansion sectional view of the pin device of the related art.
Figure 9:
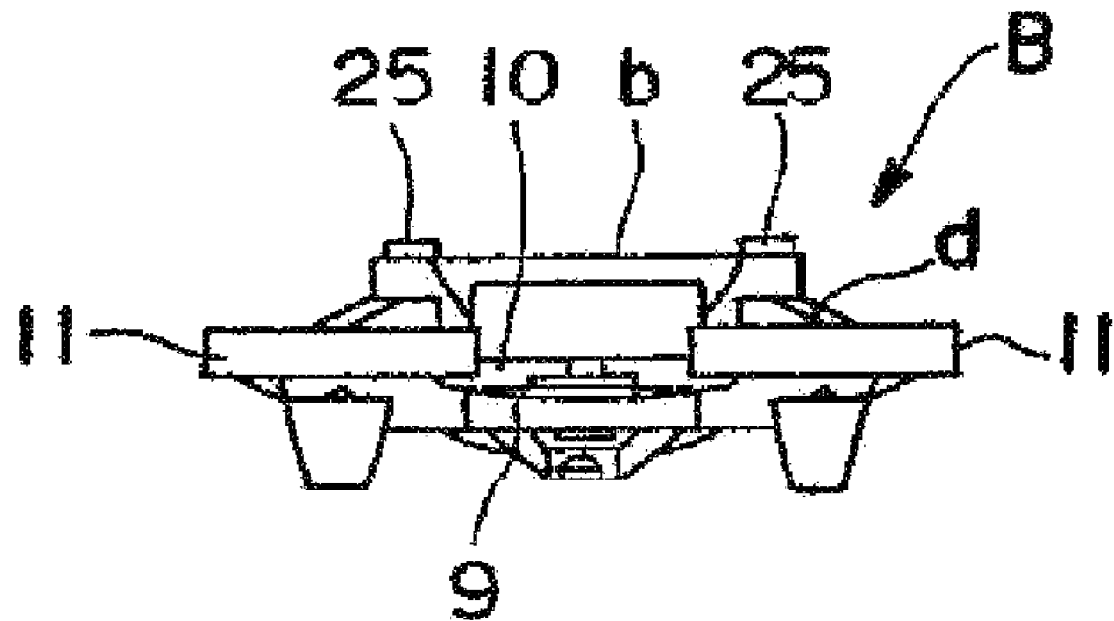
FIG. 9 is a right side view of the lower jaw plate B of the related art.
Figure 10:
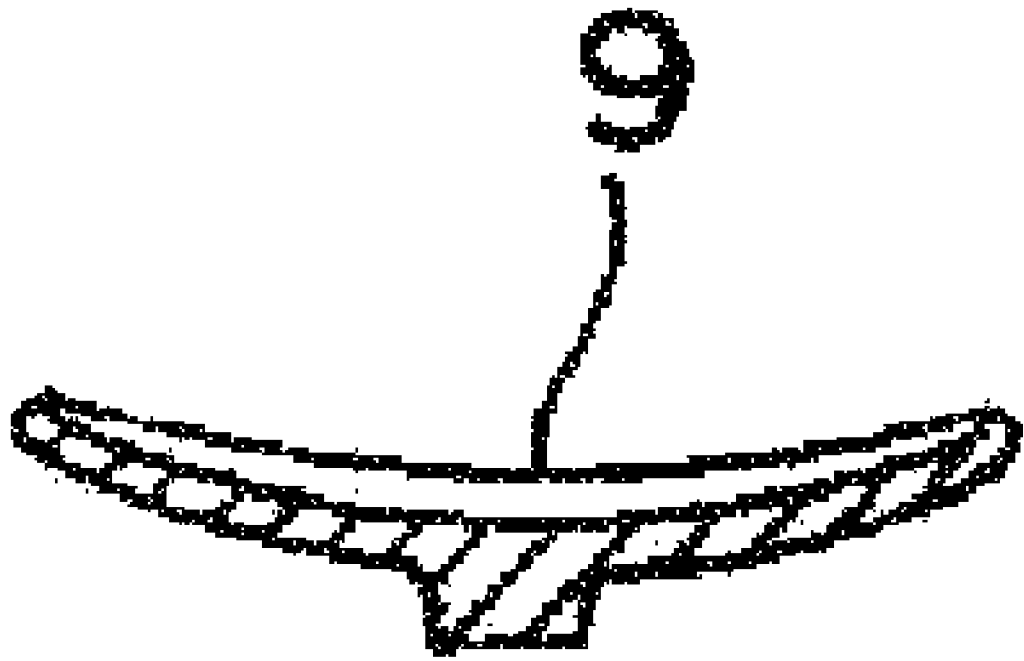
FIG. 10 is a section view of the tracing plate of the related art.
Figure 11:
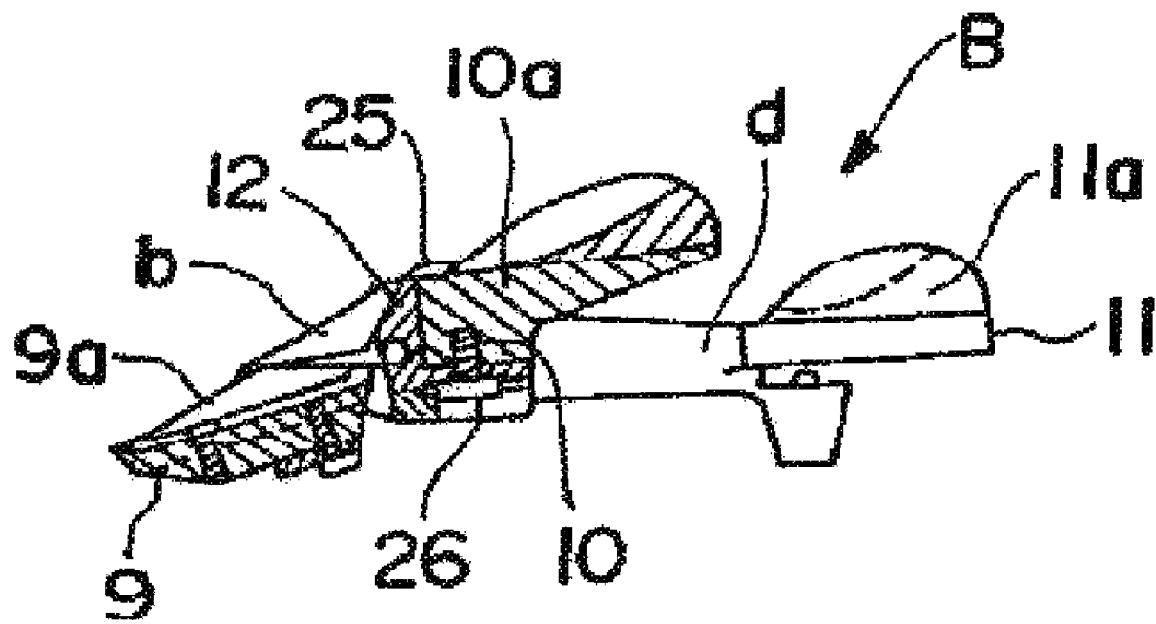
FIG. 11 is a section view where the tracing plate, the guide plate, and the jaw movement lines are formed on the surface of the lower jaw plate B of the related art.
Figure 12:
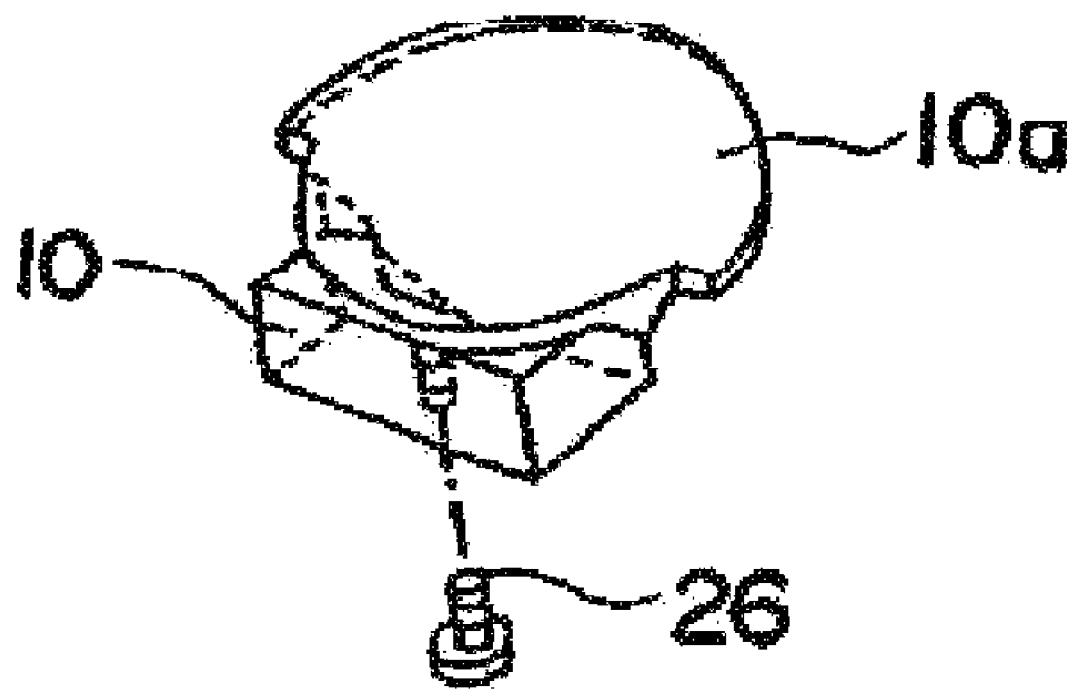
FIG. 12 is a perspective view of the guide plate of the related art.
Figure 13:
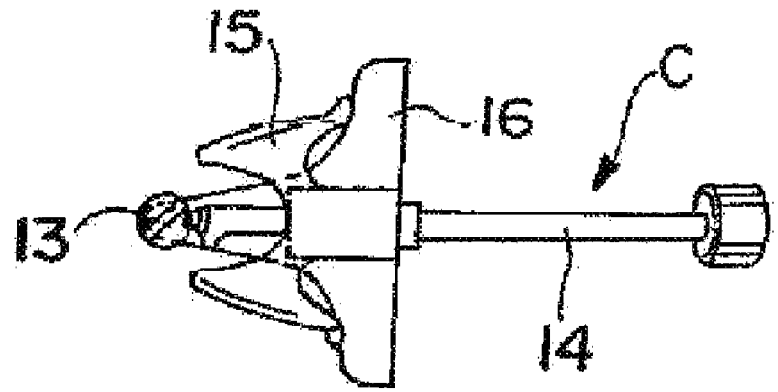
FIG. 13 (a) shows a plane view of the coupling tool, and FIG. 13 (b) shows a front view of the coupling tool of the related art.
Figure 13:
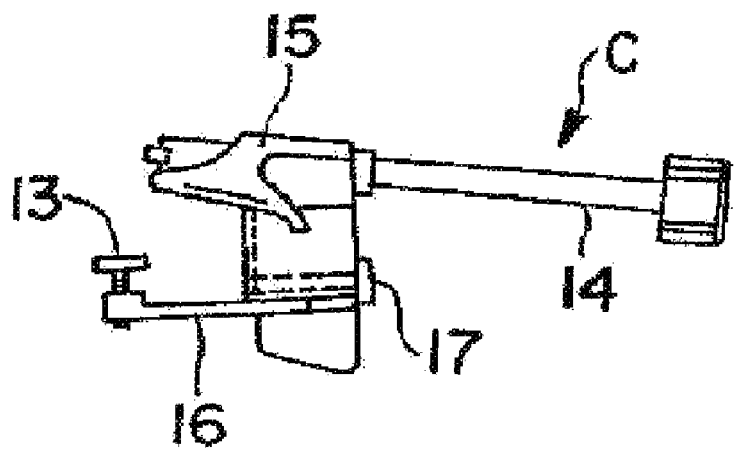
Figure 14:
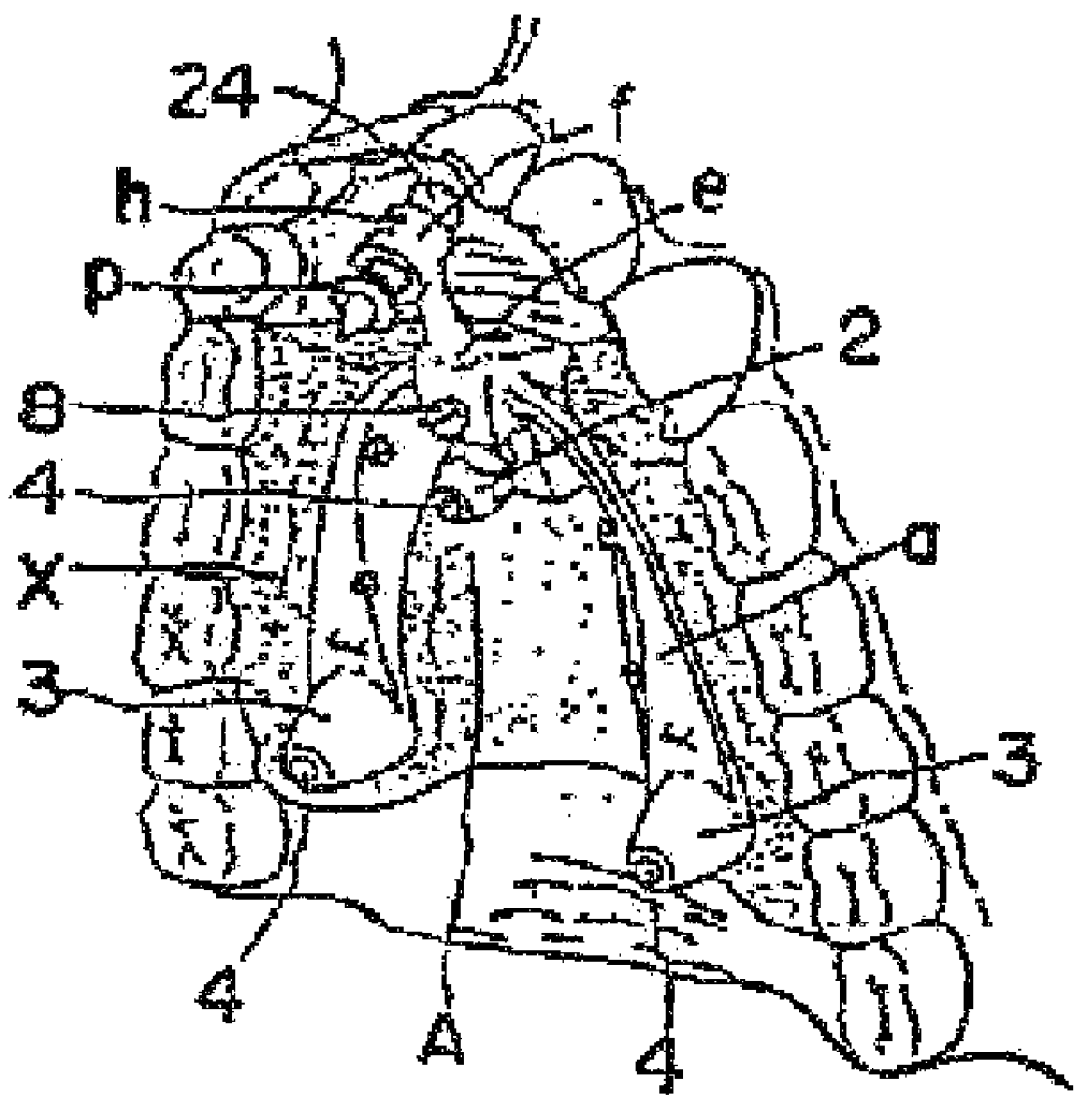
FIG. 14 is a perspective view which shows the position in the upper jaw of the upper jaw plate of the related art.
Figure 15:
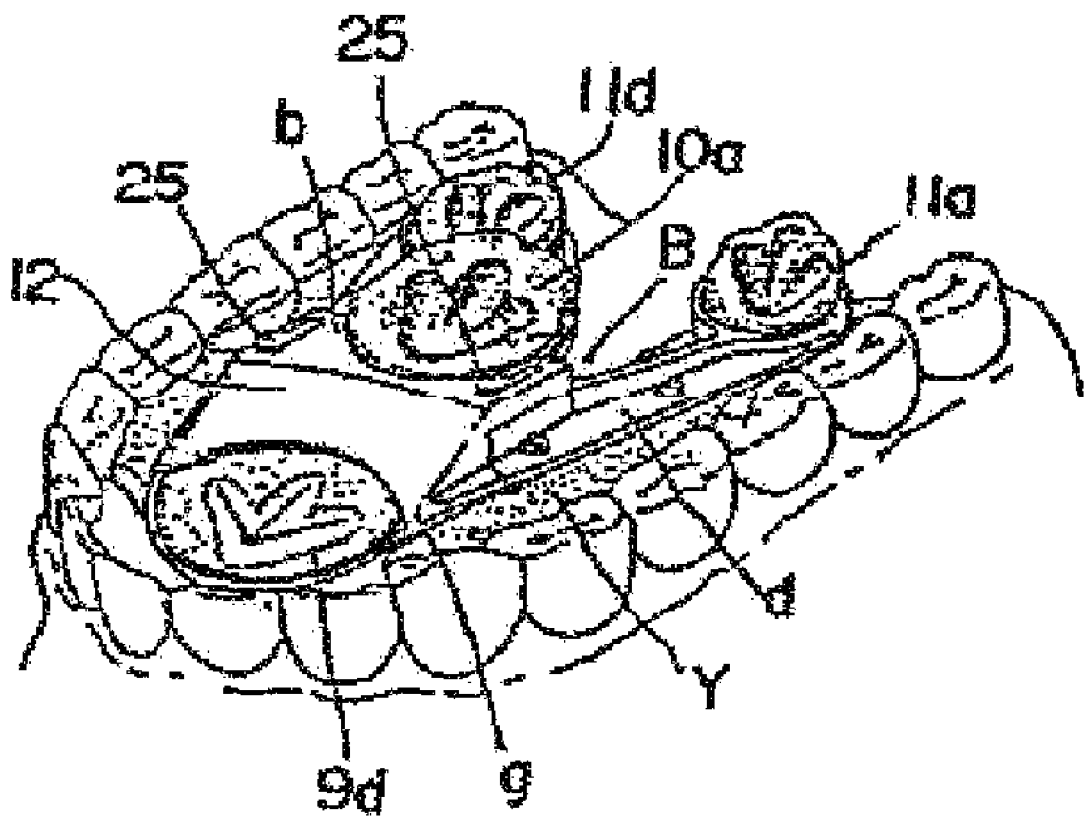
FIG. 15 is a perspective view which shows the position in the lower jaw of the lower jaw plate of the related art.
Figure 16:
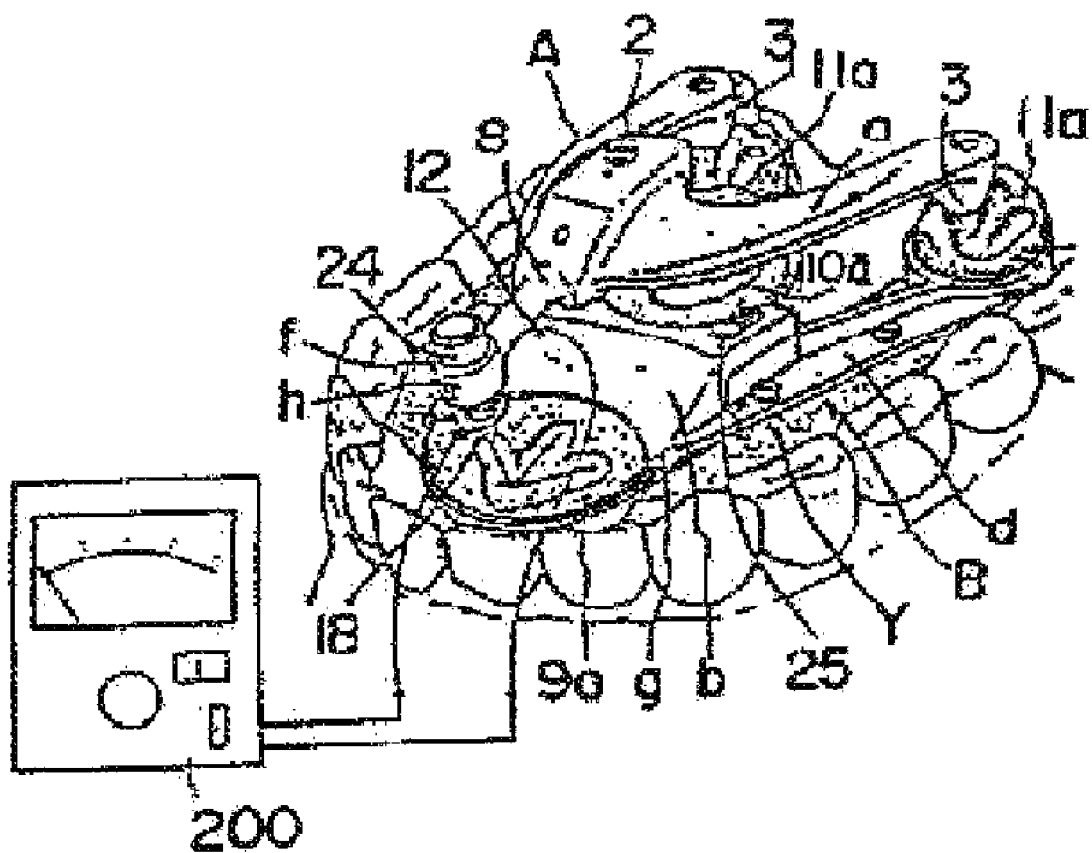
FIG. 16 is a pattern diagram that shows the connection with the electric detector of the related art.

The lower jaw plate B shown in FIGS. 5 (*a*), (*b*) can include the guide tracing table 33, and the connection pores 36*a*, and 36*b* made of (or associated with) a magnetic material which connect with the coupling tool C at the center of the U-shaped main body "b" of the lower jaw plate. Each movement line formation tables 11 can be in symmetry at the rear end of the U-shaped main body "b" of the lower jaw plate. In FIG. 5 (*b*), the guide tracing table part 33 can be detachably installed on the upper part of the connection pores 36*a*, 36*b* via magnetic force.

The guide tracing table part 33 can be integrated with the guide table part 33*a* of the rear part, and the tracing table part 33*b* of the front part. The inducement guide plate made of plastic is put on the guide table part 33*a*, which makes it correspond to the guide prop stud 2 of the upper jaw plate A. The tracing plate 34 made of plastic is put on the tracing table part 33*b*, and each operation is done by making it correspond to the tracing pin 1 in the Gothic arch tracing process, and to the jaw fixation pin in the Check-bite collection process.

The tracing material, such as a plastic material, putty silicone rubber, etc., is put on the above-mentioned movement line formation table 11 which corresponds to the movement line formation auxiliary studs 3 of the upper jaw plate A in the movement line formation process. The tracing material touches with the studs 3 for making the movement line record 11*a* by sculpturing and recording thereof.

Figure 17:
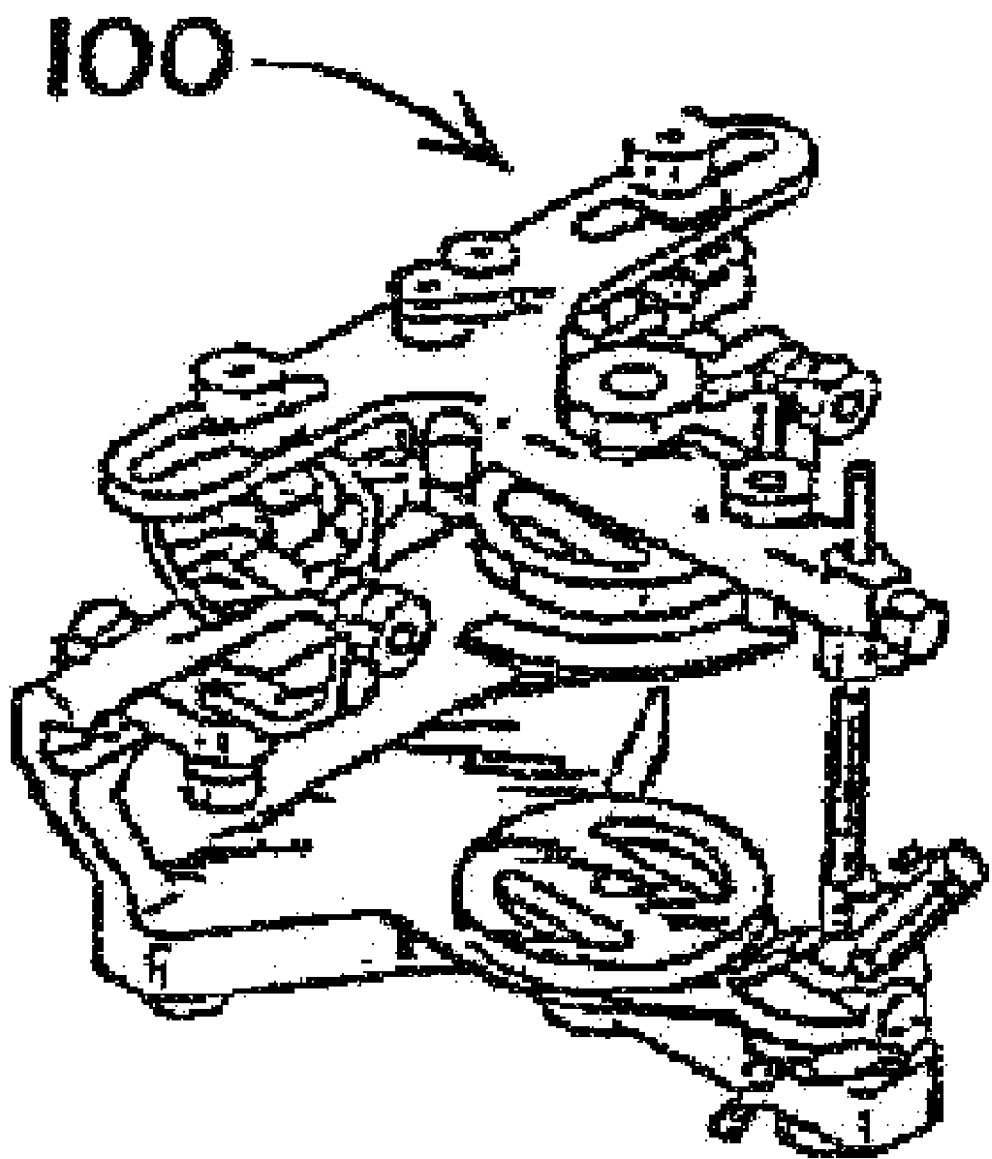
FIG. 17 is a perspective view which shows the adjustable occlusion device.

The coupling tool C shown in FIG. 1(*c*) can include the upper jaw plate connection part 29 having studs 31*a*, 31*b* for connecting with the upper jaw plate A, the lower jaw plate connection part 30 having studs 32*a*, 32*b*, 32*c* for connecting with the lower jaw plate B, and the fixation screw 17 of the plate interval for connecting the upper jaw plate connection part 29 and the lower jaw plate connection part 30. This coupling tool C connects the upper jaw plate A with the lower jaw plate B, and adjusts the upper jaw plate A and the record floor X, as well as the lower jaw plate B and the record floor Y to be at the starting position and stabilized at an upper, lower and horizontal position. As these are fixed at once with the bond agent such as the polymerization resin after being adjusted to be in the best position, they are used for deciding the position together with the adjusting occlusion machine 100 (see FIG. 17) in the connection process, and the adjustment uniting process.

After these processes, in the connection release process of resolving the upper jaw plate A and the lower jaw plate B, the upper jaw plate connection part 29 and the lower jaw plate connection part 30 can be separated by loosening the plate interval fixation screw 17, and the connection release can be done in a short time. As a part of, or the whole of the connection pore 27, stud installation pore 28, tracing pin installation pore 40 installed in the upper jaw plate A, and a part of, or the whole of the connection pore 36*a*, 36*b* installed in the lower jaw plate B can be formed with a magnetic material or associated with a magnetic force. Thus, the work of the tracing operation in the above-mentioned mouth cavity can be easily done in short time.

Since a part or the whole of the connection pore 27 installed in the above-mentioned upper jaw plate A, the stud installation pore 28, the installation pore 40 of the tracing pin 1, and the connection pore 36*a*, 36*b* installed in the above-mentioned lower jaw plate B can be formed with (or associated with) a magnetic material, and screws are not necessarily used, each work of the tracing operation in the in-mouth cavity is easy and can be done in a short time.

Moreover, since the materials such as pins 1 etc., can be made of or associated with a magnetic material, safer and quicker operation can be accomplished. In the past, the screws were clamped by hand, and were integrated on the resin plate by using a lot of screws, resulting in a less safe operation. Concretely, easy detaching processes can be accomplished, and a complex operation such as tightening the screw in each exchange is not required, since the tracing pin 1, and the jaw fixing pin (tracing pin used together) can be fixed respectively to the tracing pin installation pore 40 (and other components can be fixed) via magnetic force.

Since the above-mentioned guide prop stud 2 can be fixed by the magnetic force of the connection pore 27, it is easy to detach them for adjusting jaw intervals, and time for the clinical adjustment is shortened because complex operation is not required. In these connection release processes, the upper jaw plate connection part 29 and the lower jaw plate connection part 30 can be separated by loosening the plate interval fixing screw 17, and those connection release processes can be done in a short time. In addition, the guide table 10, and the tracing table 9 are combined together as the guide tracing table 33 which were separately installed in the lower jaw plate B in the past, whereby the detaching process can be done at one time. In addition, detaching can be easy because installation with the lower jaw plate B can be accomplished via fixing with the magnetic force associated with the connection pore 36*a*, 36*b*. Therefore, each material in the mouth cavity can be quickly detached in the positioning process, the record formation process of the guide plate 10*a* in the clinic, the record formation process of the tracing plate 9*a*, the Gothic arch tracing process, and Check-bite collection process.

Moreover, in the tracing table 33*b* placed forward of the guide tracing table 33, the turning on of electricity via contact between the tracing pin 1 and metallic tracing plate 34 is able to be detected. And, when a small hole in the Check-bite collection process cannot be confirmed by interruption of the front teeth, it can be confirmed by electric detector 200 with lights, buzzer sounds, etc.

While there has been described what are considered to be exemplary embodiments of the disclosed subject matter, it will be understood that various modifications may be made thereto, and it is intended that the appended claims cover all such modifications as fall within the true spirit and scope of the invention.

What is claimed is:

1. An in mouth cavity tracing device, comprising:
   an upper jaw plate having a substantially U-shaped main body, the upper jaw plate including a guide prop stud, a tracing pin, and at least two auxiliary studs;
   a lower jaw plate having a substantially U-shaped main body; and
   a coupling tool which connects the upper jaw plate and lower jaw plate, wherein
   the upper jaw plate includes a connection pore formed downward and having an opening located substantially at a center of the U-shaped main body of the upper jaw plate and configured to connect to the guide prop stud,
   the upper jaw plate includes a tracing pin installation pore formed downward and having an opening configured to connect to the tracing pin at a front of the main body of the upper jaw plate, and
   the two auxiliary studs are configured to record movement lines and project in substantial symmetry respectively downward at a rear of the main body of the upper jaw plate, wherein
   the lower jaw plate includes a guide tracing table configured to be positioned at a substantial center of the U shaped main body of the upper jaw plate when the upper jaw plate is connected to the lower jaw plate, and the lower jaw plate includes movement line formation tables located at a rear of the U shaped main body of the lower jaw respectively in substantial symmetry, and the coupling tool includes an upper jaw plate connection part having a plurality of studs configured to connect with the upper jaw plate, and a lower jaw plate connection part including another stud configured to connect with the lower jaw plate, the upper jaw plate connection part includes a portion extending in an opposed relationship with respect to the studs and configured to mate with the lower jaw plate connection part, and a plate interval fixing screw configured to connect the upper jaw plate connection part with the lower jaw plate connection part and configured to release the upper jaw plate connection part from the lower jaw plate connection part when rotated a predetermined amount, and at least a part of at least one of the upper jaw plate connection pore and the upper jaw plate tracing pin installation pore includes a first magnetic material, and at least a respective one of a part of the guide prop stud and a part of the tracing pin includes a second magnetic material configured such that the first magnetic material is magnetically attracted to the second magnetic material and such that a retaining force exists between the first magnetic material and second magnetic material to retain the at least respective one of a part of the guide prop stud and a part of the tracing pin within a respective one of the upper jaw plate connection pore and the upper jaw plate tracing pin installation pore, and wherein the at least one of a part of the guide prop stud and a part of the tracing pin is configured to closely mate with and extend into a respective one of the upper jaw plate connection pore and the upper jaw plate tracing pin installation pore.

2. The in mouth cavity tracing device according to claim 1, further comprising:

a lower jaw inducement guide plate made of plastic and shaped to include thee dimensional slopes, and wherein the guide tracing table and lower jaw inducement guide plate are configured to be tightly attached, and fitted to be freely attachable/detachable.

3. The in mouth cavity tracing device described in claim 1, further comprising:

an auxiliary tool having two pins located adjacent a side wall that has at least one ditch located therein, and wherein the guide tracing table and the lower jaw plate connection part are configured to mate with the main body of the lower jaw plate.

4. The in mouth cavity tracing device according to claim 1, further comprising:

a plurality of lower jaw inducement guide plates made of plastic and shaped to include three dimensional slopes having angles of 20-50 degrees, and the plurality of lower jaw inducement guide plates are fitted and configured to be selectively attachable/detachable to the guide tracing table.

5. The in mouth cavity tracing device described in claim 2, further comprising:

an auxiliary tool having two pins located adjacent a side wall that has at least one ditch located therein, and wherein the guide tracing table and the lower jaw plate connection part are configured to mate with the main body of the lower jaw plate.

6. The in mouth cavity tracing device according to claim 2, further comprising:

a plurality of lower jaw inducement guide plates includes three dimensional slopes having angles of 20-50 degrees, and the lower jaw inducement guide plates being fitted and configured to be selectively attachable/detachable to the guide tracing table.

7. The in mouth cavity tracing device described in claim 1, wherein at least a portion of at least one of the upper jaw plate connection pore and the upper jaw plate tracing pin installation pore is made of a magnetic material.

8. The in mouth cavity tracing device described in claim 1, wherein at least a part of one of the tracing pin and the guide stud includes a magnetic material.

9. The in mouth cavity tracing device described in claim 1, wherein the lower jaw plate includes a connection pore that includes a magnetic material.

10. An in mouth cavity tracing device, comprising:

an upper jaw plate including a pin installation portion, a stud connection portion located adjacent the pin installation portion, and two line formation portions located adjacent the pin installation portion;

a drawing pin configured to be attached to the pin installation portion;

a guide prop stud configured to be attached to the stud connection portion;

a lower jaw plate including a trace plate portion, an inducement plate portion located adjacent the trace plate portion, and two line formation portions located adjacent the inducement plate portion; and a coupling tool which connects the upper jaw plate and lower jaw plate, wherein the coupling tool includes an upper jaw plate connection part having at least one stud configured to connect with the upper jaw plate, and a lower jaw plate connection part including another stud configured to connect with the lower jaw plate, the upper jaw plate connection part includes a portion configured to mate with the lower jaw plate connection part, and a plate interval fixing screw configured to connect the upper jaw plate connection part with the lower jaw plate connection part and configured to release the upper jaw plate connection part from the lower jaw plate connection part when rotated a predetermined amount, a spring located between the screw and the lower jaw plate connection part to facilitate connection of the screw with the upper jaw plate connection part, wherein at least one of the drawing pin, guide prop stud, pin installation portion, and stud connection portion includes a first magnetic material, and at least another of the drawing pin, guide prop stud, pin installation portion, and stud connection portion includes a second magnetic material portion configured such that the first magnetic material portion is magnetically attracted to the second magnetic material portion and such that a retaining force exists between the first magnetic material and second magnetic material to retain either the drawing pin within a concave pore defined in the pin installation portion or the guide prop stud within a concave pore defined in the stud connection portion.

11. The in mouth cavity tracing device of claim 10, further comprising:

an auxiliary tool having two pins located adjacent a side wall that has at least one ditch located therein, and wherein the trace plate portion and the lower jaw plate connection part are configured to mate with the lower jaw plate.

12. The in mouth cavity tracing device of claim 10, further comprising:

line formation tables located on the line formation portions of the lower jaw plate.

13. The in mouth cavity tracing device of claim 10, further comprising:
line formation studs located on the line formation portions of the upper jaw plate.

14. The in mouth cavity tracing device of claim 10, wherein the stud connection portion is formed as an opening in the upper jaw plate.

15. The in mouth cavity tracing device of claim 10, wherein the pin installation portion is formed as an opening in the upper jaw plate.

16. The in mouth cavity tracing device of claim 10, further comprising:
a plurality of inducement guide tables.

17. The in mouth cavity tracing device of claim 10, further comprising:
an electronic notification device electrically connected to one of the drawing pin and the trace plate portion and configured to communicate when the drawing pin comes into contact with the trace plate portion.

18. The in mouth cavity tracing device of claim 10, wherein the drawing pin, the guide prop stud, the pin installation portion, and the stud installation portion include magnetic material.

19. The in mouth cavity tracing device of claim 10, wherein the lower jaw plate includes at least one guide tracing table pore that includes a magnetic material.

* * * * *